United States Patent
Nachman et al.

(10) Patent No.: US 7,603,158 B2
(45) Date of Patent: Oct. 13, 2009

(54) CURRENT DENSITY IMPEDANCE IMAGING (CDII)

(76) Inventors: Adrian Nachman, 23 Rose Park Drive, Toronto (CA) M4T 1R2; Michael L. G. Joy, 8 Ross Street, Toronto (CA) M5T 1Z9; Karshi F. Hasanov, 326 Sunnyside Ave., Toronto (CA) M6R 2R4; Richard S. Yoon, 750 Bay Street, Apt. 2107, Toronto (CA) M5G 1N6

( * ) Notice: Subject to any disclaimer, the term of this patent is extended or adjusted under 35 U.S.C. 154(b) by 483 days.

(21) Appl. No.: 10/933,508

(22) Filed: Sep. 3, 2004

(65) Prior Publication Data

US 2005/0054911 A1  Mar. 10, 2005

Related U.S. Application Data

(60) Provisional application No. 60/499,734, filed on Sep. 4, 2003.

(51) Int. Cl.
*A61B 5/05* (2006.01)

(52) U.S. Cl. .................. 600/411; 600/547; 600/410; 600/425; 324/323; 324/326; 324/347; 324/600

(58) Field of Classification Search .............. 600/407, 600/411, 547, 425, 410; 324/307, 309, 323–326, 324/347, 354, 357, 600
See application file for complete search history.

(56) References Cited

U.S. PATENT DOCUMENTS

| | | | | |
|---|---|---|---|---|
| 5,964,705 | A | * | 10/1999 | Truwit et al. ........... 600/423 |
| 6,201,990 | B1 | * | 3/2001 | Wexler et al. .......... 600/547 |
| 6,397,095 | B1 | | 5/2002 | Eyuboglu |
| 6,720,768 | B2 | * | 4/2004 | Crozier et al. ......... 324/318 |
| 7,092,748 | B2 | * | 8/2006 | Sosa et al. ............. 600/407 |

(Continued)

FOREIGN PATENT DOCUMENTS

CA  2480430  *  3/2005

OTHER PUBLICATIONS

GC Scott, MLG Joy, RL Armstrong, RM Henkelman. Measurement of Nonuniform Current Density by Magnetic Resonance. IEEE Trans. Med. Imag. 10(3): Sep. 1991: pp. 362-374.*

(Continued)

*Primary Examiner*—Brian Casler
*Assistant Examiner*—Amanda L Lauritzen
(74) *Attorney, Agent, or Firm*—Hill & Schumacher; Lynn C. Schumacher

(57) ABSTRACT

A method for non-invasive mapping (imaging) of the electrical impedance of an object. The present invention provides a method, current density impedance imaging (CDII) which produces an impedance image of object by measuring current density distributions and directly calculating the local impedance values. The method includes making measurements of at least two current density vector fields, $J_1$ and $J_2$, within a region of interest in an object and then calculating the logarithmic gradient of local conductivity, $\nabla \ln \sigma(x,y,z)$, using a formula $$\nabla \ln \sigma = \frac{(\nabla \times J_2) \cdot (J_1 \times J_2)}{|J_1 \times J_2|^2} J_1 + \frac{(\nabla \times J_1) \cdot (J_2 \times J_1)}{|J_1 \times J_2|^2} J_2 + \frac{(\nabla \times J_1) \cdot J_2}{|J_1 \times J_2|^2} J_1 \times J_2 \quad (1)$$

where $\vec{J}_1(x,y,z)$ and $\vec{J}_2(x,y,z)$, are the pair of measured nonparallel current densities at point (x,y,z) and $\nabla$ denotes the gradient operator.

27 Claims, 8 Drawing Sheets

U.S. PATENT DOCUMENTS

| | | | |
|---|---|---|---|
| 7,169,107 B2* | 1/2007 | Jersey-Willuhn et al. | 600/442 |
| 7,256,582 B2* | 8/2007 | Gorek et al. | 324/373 |
| 2003/0109871 A1* | 6/2003 | Johnson et al. | 606/42 |
| 2003/0216630 A1* | 11/2003 | Jersey-Willuhn et al. | 600/407 |
| 2004/0162501 A1* | 8/2004 | Imran | 600/547 |
| 2004/0242989 A1* | 12/2004 | Zhu et al. | 600/407 |
| 2005/0107719 A1* | 5/2005 | Arad (Abbound) | 600/547 |
| 2006/0085049 A1* | 4/2006 | Cory et al. | 607/48 |
| 2006/0224061 A1* | 10/2006 | Woo et al. | 600/410 |
| 2007/0088210 A1* | 4/2007 | Woo et al. | 600/410 |
| 2007/0288064 A1* | 12/2007 | Butson et al. | 607/45 |

OTHER PUBLICATIONS

BM Eyuboglu, R Reddy, JS Leigh. Imaging Electrical Current Density Using Nuclear Magnetic Resonance. ELEKTRIK 6(3): 1998: pp. 201-214.*

D Isaacson, JC Newell, GJ Saulnier. Electrical Impedance Imaging. Proceedings of the 26th Annual International Conference of the IEEE EMBS: San Fancisco, CA: Sep. 2004: pp. 3573-3575.*

KF Hasanov, AW Ma, RS Yoon, Al Nachman, ML Joy. A New Approach to Current Density Impedance Imaging. Proceedings of the 26th Annual International Conference of the IEEE EMBS: San Francisco, CA: Sep. 2004: pp. 1321-1324.*

O Ozbek, O Birgul, BM Eyuboglu, YZ Ider. Imaging Electrical Current Density Using 0.15T Magnetic Resonance Imaigng System. Proceedings of the $23^{rd}$ Annual EMBS International Conference: Istabul, Turke: Oct. 2001: pp. 2292-2295.*

High fidelity imaing and high performance computing in nonlinear EIT. BH Blott, SJ Cox, GJ Daniell, MJ Caton, DA Nicole. Physiol. Meas. 21: pp. 7-13. Jul. 16, 1999.*

A new approach to current density impedance imaging. KF Hasanov, AW Ma, RS Yoon, Al Nachman, ML Joy. Proceedings of the $26^{th}$ Annual International Conference of the IEEE EMBS. Sep. 2004.*

MR current density and conductivity imaging: The state of the art. MLG Joy. Proceedings of the $26^{th}$ Annual International Conference of the IEEE EMBS. Sep. 2004.*

Equipotential line method for magnetic resonance electrical impedance tomography. O Kwon, J-Y Lee, J-R Yoon. Institute of Physics Publishing: Inverse Problems 18: pp. 1089-1100. 2002.*

* cited by examiner

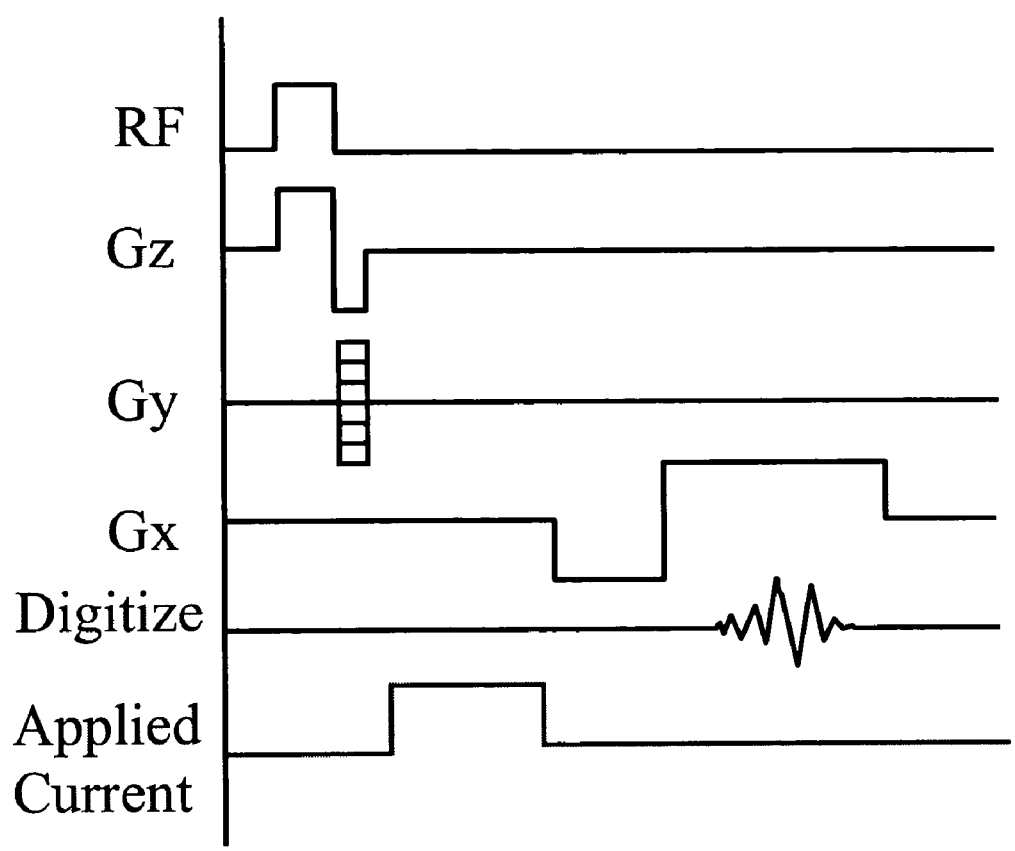
Figure 4b An MRI Pulse Sequence for measuring applied current.

CURRENT DENSITY IMPEDANCE IMAGING (CDII)

CROSS REFERENCE TO RELATED U.S. PATENT APPLICATIONS

This patent application claims the priority benefit from U.S. Provisional Patent Application Ser. No. 60/499,734 filed on Sep. 4, 2003 entitled Current Density Impedance Imaging (CDII), and which is incorporated herein in its entirety.

FIELD OF INVENTION

The present invention relates to a non-invasive mapping (imaging) of the electrical impedance of an object.

BACKGROUND OF THE INVENTION

Electrical impedance tomography (EIT) is a technique that maps (images) the electrical impedance of an object non-invasively. EIT calculates internal impedance (or conductivity) of the object by applying a known electric current through its surface and then measuring the resulting surface potentials. Although numerous surface electrodes (sometimes hundreds) are used during the procedure, EIT suffers from an inherent low spatial resolution due to the ill-posed nature of the problem. Therefore, EIT has not been widely accepted as a clinical imaging tool.

More recently, there have been efforts to combine EIT with magnetic resonance imaging (MRI) to improve the performance. However, these techniques require complete electrical measurement information from all points inside the object in order to calculate the impedance at a given point within the object. Therefore, these global methods fail when there are areas of missing information inside the object (FIG. 1a on right).

U.S. Pat. No. 6,397,095 B1, issued May 28, 2002 discloses a magnetic resonance-electrical impedance tomography (MREIT) technique for determining the local conductivity of an object. This technique combines magnetic resonance current density imaging (MRCDI) with electrical impedance tomography (EIT). MREIT technique includes a step of current density imaging by placing a series of electrodes around the patient or object to be imaged for the application of current, placing the patient or object in a strong magnetic field, and applying an MR imaging sequence which is synchronized with the application of current through the electrodes. The electric potentials of the surface of the object or patient are measured simultaneously with the MR imaging sequence, as in EIT and the MR imaging signal containing information about the current and the measured potential are processed to calculate the internal impedance of the object or patient. Specifically, the measurements of surface potentials and equipotential lines are used to compute the impedance.

SUMMARY OF THE INVENTION

The present invention provides a method of non-invasive imaging of electrical impedance of an object, comprising the steps of:
a) making measurements of at least two nonparallel current density vector fields, $\vec{J}_1(x,y,z)$ and $\vec{J}_2(x,y,z)$, within a region of interest in the object by utilizing an apparatus for inducing current in the object and simultaneously using a magnetic resonance imaging (MRI) system to synchronously apply a magnetic resonance imaging sequence to the object and using image data detected by the MRI system to measure a magnetic field created by the current induced in the object, and using a computer device to calculate said at least two nonparallel current density vector fields, $\vec{J}_1(x,y,z)$ and $\vec{J}_2(x,y,z)$;
b) utilizing a computer device to directly calculate, without iteration a logarithmic gradient of local conductivity, $\nabla \ln\sigma(x,y,z)$, within the region of interest without requiring an electric potential value using a formula $$\nabla \ln\sigma = \frac{(\nabla \times J_2) \cdot (J_1 \times J_2)}{|J_1 \times J_2|^2} J_1 + \frac{(\nabla \times J_1) \cdot (J_2 \times J_1)}{|J_1 \times J_2|^2} J_2 + \frac{(\nabla \times J_1) \cdot J_2}{|J_1 \times J_2|^2} J_1 \times J_2 \quad (1)$$

where $J_1 = \vec{J}_1(x,y,z)$, $J_2(x,y,z)$, and $\nabla \ln\sigma = \nabla \ln\sigma(x,y,z)$, and where $J_1$ and $J_2$ are a pair of measured nonparallel current densities at point $(x,y,z)$ and $\nabla$ denotes a gradient operator; and
c) producing a conductivity image based on the calculated logarithmic gradient of local conductivity within the region of interest.

In this aspect of the invention the method may include calculating a relative conductivity $$\sigma_R(x, y, z) = \frac{\sigma(x, y, z)}{\sigma(x_0, y_0, z_0)},$$

between any two points $(x,y,z)$ and $(x_0,y_0,z_0)$ from $\nabla \ln \sigma(x,y,z)$ by integration along any path joining the two points along which $\nabla \ln \sigma(x,y,z)$ has been determined using a formula for $\sigma_R(x,y,z)$ given by:

$$\sigma_R(x, y, z) = \exp\left(\int_{(x_0,y_0,z_0)}^{(x,y,z)} \nabla \ln\sigma\right). \quad (2)$$

In another aspect of the invention there is provided a method of non-invasive imaging of electrical impedance of an object. The method includes the steps of:
a) affixing a sufficient number of current conducting electrodes to a surface of the object so that at least two sets of current distribution are created inside the object, the current conducting electrodes being connected to a current generator;
b) placing the object inside a magnetic field generated by a magnetic resonance (MR) imager magnet for MR imaging;
c) during the MR imaging, inducing current flow in an interior of the object by applying current between a first pair of current conductors synchronously with an effective current imaging sequence which encodes a strength of an extra magnetic field arising from the current flow induced inside the object, the extra magnetic field component being encoded as a part of a complex MR image;
d) acquiring the resulting complex MR images through the use of a MR imaging sequence and transferring the resulting complex MR images to a computer;
e) processing the complex MR images to calculate a current density vector field $\vec{J}_1(x,y,z)$ within a region of interest in the object;

f) repeated repeating steps c), d) and e) at least once more to measure the current density vector field $\vec{J}_2(x,y,z)$ within the region of interest for at least one other combination of current electrodes; and g) utilizing a computer device to directly calculate, without iteration, a logarithmic gradient of local conductivity, $\nabla \ln\sigma(x,y,z)$, within the region of interest without requiring an electric potential value, using a formula:

$$\nabla \ln\sigma = \frac{(\nabla \times J_2)\cdot(J_1 \times J_2)}{|J_1 \times J_2|^2} J_1 + \frac{(\nabla \times J_1)\cdot(J_2 \times J_1)}{|J_1 \times J_2|^2} J_2 + \frac{(\nabla \times J_1)\cdot J_2}{|J_1 \times J_2|^2} J_1 \times J_2 \quad (1)$$

where $J_1 = \vec{J}_1(x,y,z)$ $J_2 = \vec{J}_2(x,y,z)$, and $\nabla \ln\sigma = \nabla \ln\sigma(x,y,z)$, and where $\vec{J}_1(x,y,z)$ and $\vec{J}_2(x,y,z)$ are a pair of measured nonparallel current densities at point (x,y,z) and $\nabla$ denotes a gradient; and h) producing a conductivity image based on the calculated logarithmic gradient of local conductivity within the region of interest.

The method also includes a method of non-invasive imaging of electrical impedance of an object, comprising the steps of:

a) making measurements of derivatives of at least two nonparallel current density vector fields, $\vec{J}_1(x,y,z)$ and $\vec{J}_2(x,y,z)$, in one direction d within a region of interest in an object when a condition $\partial_d \nabla \sigma = 0$ is satisfied, by utilizing an apparatus for inducing current in the object and simultaneously using a magnetic resonance imaging (MRI) system to synchronously apply a magnetic resonance imaging sequence to the object and using image data detected by the MRI system to measure a magnetic field created by the current induced in the object, and using a computer device to calculate said at least two nonparallel current density vector fields, $\vec{J}_1(x,y,z)$ and $\vec{J}_2(x,y,z)$;

b) utilizing a computer device to directly calculate, without iteration, the logarithmic gradient of local conductivity, $\nabla \ln \sigma(x,y,z)$, at that point within the region of interest without requiring an electric potential value, using a formula $$\nabla \ln\sigma = \frac{(\nabla \times \partial_d J_2)\cdot(\partial_d J_1 \times \partial_d J_2)}{|\partial_d J_1 \times \partial_d J_2|^2} \partial_d J_1 + \frac{(\nabla \times \partial_d J_1)\cdot(\partial_d J_2 \times \partial_d J_1)}{|\partial_d J_1 \times \partial_d J_2|^2} \partial_d J_2 + \frac{(\nabla \times \partial_d J_1)\cdot \partial_d J_2}{|\partial_d J_1 \times \partial_d J_2|^2} \partial_d J_1 \times \partial_d J_2 \quad (5)$$

where $J_1 = \vec{J}_1(x,y,z)$, $J_2 = \vec{J}_2(x,y,z)$, and $\nabla \ln\sigma = \nabla \ln\sigma(x,y,z)$, and where $\partial_d$ denotes a directional derivative in a direction d, and $\partial_d J_1$ and $\partial_d J_2$ are a pair of measured derivatives of the current density vector fields in the direction d at a point (x,y,z), and $\nabla$ denotes a gradient operator; and c) producing a conductivity image based on the calculated logarithmic gradient of local conductivity within the region of interest.

BRIEF DESCRIPTION OF THE DRAWINGS

In order that the invention may be better understood, preferred embodiments will now be described by way of example only, with reference to the accompanying drawings, wherein.

FIG. 4a shows a block diagram of the current density imaging (CDI) technique which utilizes magnetic resonance imager to measure current density at points within the object, the CDI system is set up by placing two or more electrodes on the surface of the object. For the present application, the current electrodes can be placed any where on the object as long as at least two sets of non parallel current distributions can be created inside the object. The object is then placed inside a strong magnetic field generated by a magnetic resonance (MR) imager magnet; current is applied by the computer controlled current generator during an MRI imaging sequence as shown in FIG. 4b. The phase image produced by the MRI system is then used to measure a component of the magnetic field created by the applied current. This process is repeated for three orientations of the object. Maxwell's equation, $\vec{J} = \nabla \times \vec{B}/\mu_0$ is then used to calculate the desired current density J.

FIG. 4b shows an MRI Pulse Sequence for measuring applied current used in the apparatus of FIG. 4a.

DETAILED DESCRIPTION OF THE INVENTION

Figure 2:
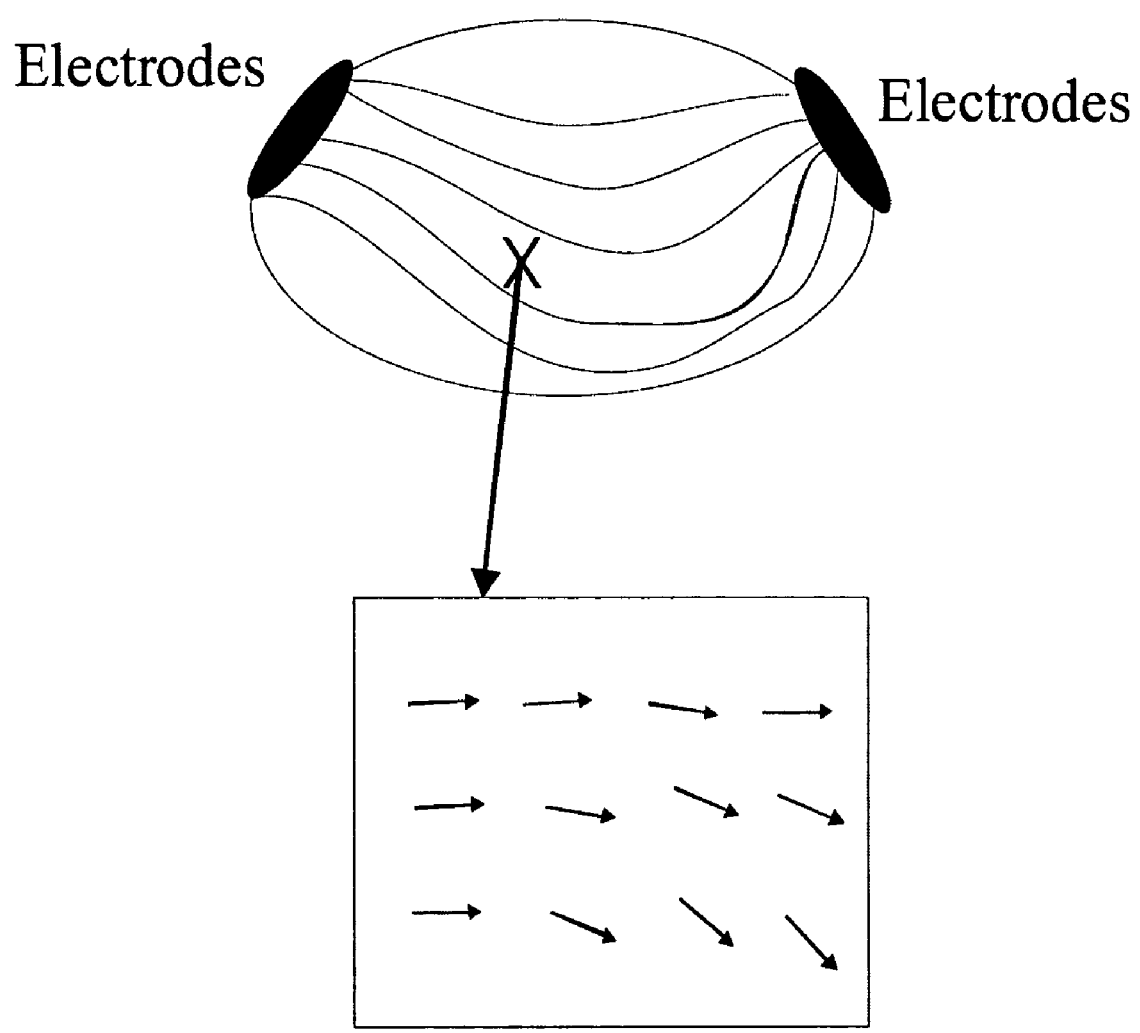
FIG. 2 shows the measured current density vectors which can be measured at locations within an object as electrical current flows from one electrode to the other.
Figure 3:
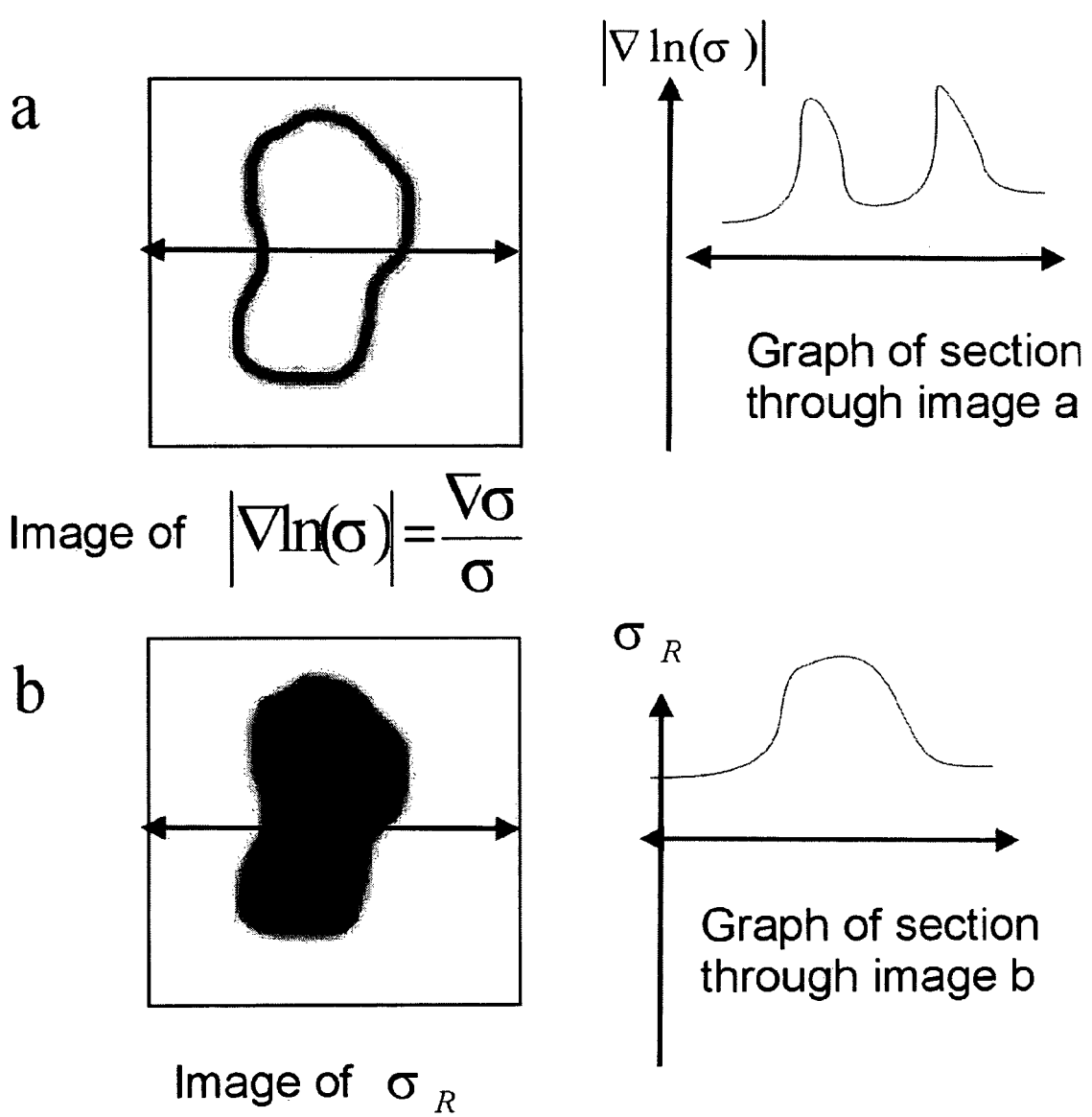
FIG. 3a shows that the image of $\nabla \ln \sigma_R(x,y,z)$ will show the boundaries of regions with different electrical conductivity.
FIG. 3b shows that the resulting image $\sigma_R(x,y,z)$ from FIG. 3a can be used to display the relative conductivity (i.e. conductivity weighted image) of the object.

Current density impedance imaging (CDII) is a new imaging technique that maps local conductivity (or impedance) of an object non-invasively. The electrical conductivity, $\sigma$, can be described by the equation, $J = \sigma E$, where J is the current density and E is the electric field. CDII requires multiple (at least two) measurements of nonparallel current density vectors, J, within the region of interest. The current density vectors indicate the current flow information at a point. For example, as the current flows from one electrode to the other, the current density vectors can be measured at locations within the object (FIG. 2). Once multiple current density vector distributions and their derivatives are measured at the same point (x,y,z), the logarithmic gradient of local conductivity, $\nabla \ln \sigma(x,y,z)$, at that point can be calculated by combining these current density vectors at each measurement point. This calculation is a novel and inventive feature of CDII and is defined by the following formula:

$$\nabla \ln \sigma = \frac{(\nabla \times J_2) \cdot (J_1 \times J_2)}{|J_1 \times J_2|^2} J_1 + \qquad (1)$$
$$\frac{(\nabla \times J_1) \cdot (J_2 \times J_1)}{|J_1 \times J_2|^2} J_2 +$$
$$\frac{(\nabla \times J_1) \cdot J_2}{|J_1 \times J_2|^2} J_1 \times J_2$$

where $\vec{J}_1(x,y,z)$ and $\vec{J}_2(x,y,z)$, are a pair of known current densities nonparallel at point (x,y,z) and $\nabla$ denotes the gradient operator. The image of $\nabla \ln \sigma(x,y,z)$ will show the boundaries of regions with different electrical conductivity (FIG. 3a and FIG. 6c).

If desired, the relative conductivity $$\sigma_R(x, y, z) = \frac{\sigma(x, y, z)}{\sigma(x_0, y_0, z_0)},$$

between any two points (x,y,z) and $(x_0,y_0,z_0)$ can be calculated from $\nabla \ln \sigma(x,y,z)$ through integration. The resulting image, $\sigma_R(x,y,z)$, can be used to display the relative conductivity (i.e. Conductivity weighted image) of the object (FIG. 3b). The integration step is along any path joining the two points along which $\nabla \ln \sigma(x,y,z)$ has been determined. The formula for $\sigma_R(x,y,z)$ can be written as:

$$\sigma_R(x, y, z) = \exp\left(\int_{(x_0,y_0,z_0)}^{(x,y,z)} \nabla \ln \sigma\right). \qquad (2)$$

In addition, the absolute value of conductivity, $\sigma(x,y,z)$, can be computed from $\sigma_R(X,y,z)$ when the $\sigma(x_0,y_0,z_0)$, the absolute value of $\sigma$, is known at some point in the region of interest. This absolute value of conductivity, $\sigma(x_0,y_0,z_0)$, can be derived from either an a priori knowledge of the object, an introduction of external agent with known conductivity (e.g. pills swallowed prior to imaging), or a surface measurement of potentials.

Another method for determining the logarithmic gradient of the electrical conductivity, $\nabla \ln \sigma$, at the point (x,y,z) utilizes only the knowledge of the derivatives of $J_1$ and $J_2$ in a given direction, if the gradient of the conductivity is constant in that direction. For example, if $\partial_z \nabla \sigma = 0$, then $\nabla \ln \sigma$ can be written as $$\nabla \ln \sigma = \frac{(\nabla \times \partial_d J_2) \cdot (\partial_d J_1 \times \partial_d J_2)}{|\partial_d J_1 \times \partial_d J_2|^2} \partial_d J_1 + \qquad (3)$$

-continued
$$\frac{(\nabla \times \partial_d J_1) \cdot (\partial_d J_2 \times \partial_d J_1)}{|\partial_d J_1 \times \partial_d J_2|^2} \partial_d J_2 +$$
$$\frac{(\nabla \times \partial_d J_1) \cdot \partial_d J_2}{|\partial_d J_1 \times \partial_d J_2|^2} \partial_d J_1 \times \partial_d J_2$$

where $\partial_d$ denotes the directional derivative in the direction d, where $\partial_d J_1$ and $\partial_d J_2$ are the pair of measured derivatives of the current density vector fields in the direction d at point (x,y,z), and $\nabla$ denotes the gradient operator. This method enables the calculation of $\nabla \ln \sigma$, without the full knowledge of the current density vectors, but just using the derivatives of the current density vectors in one direction.

Figure 1:
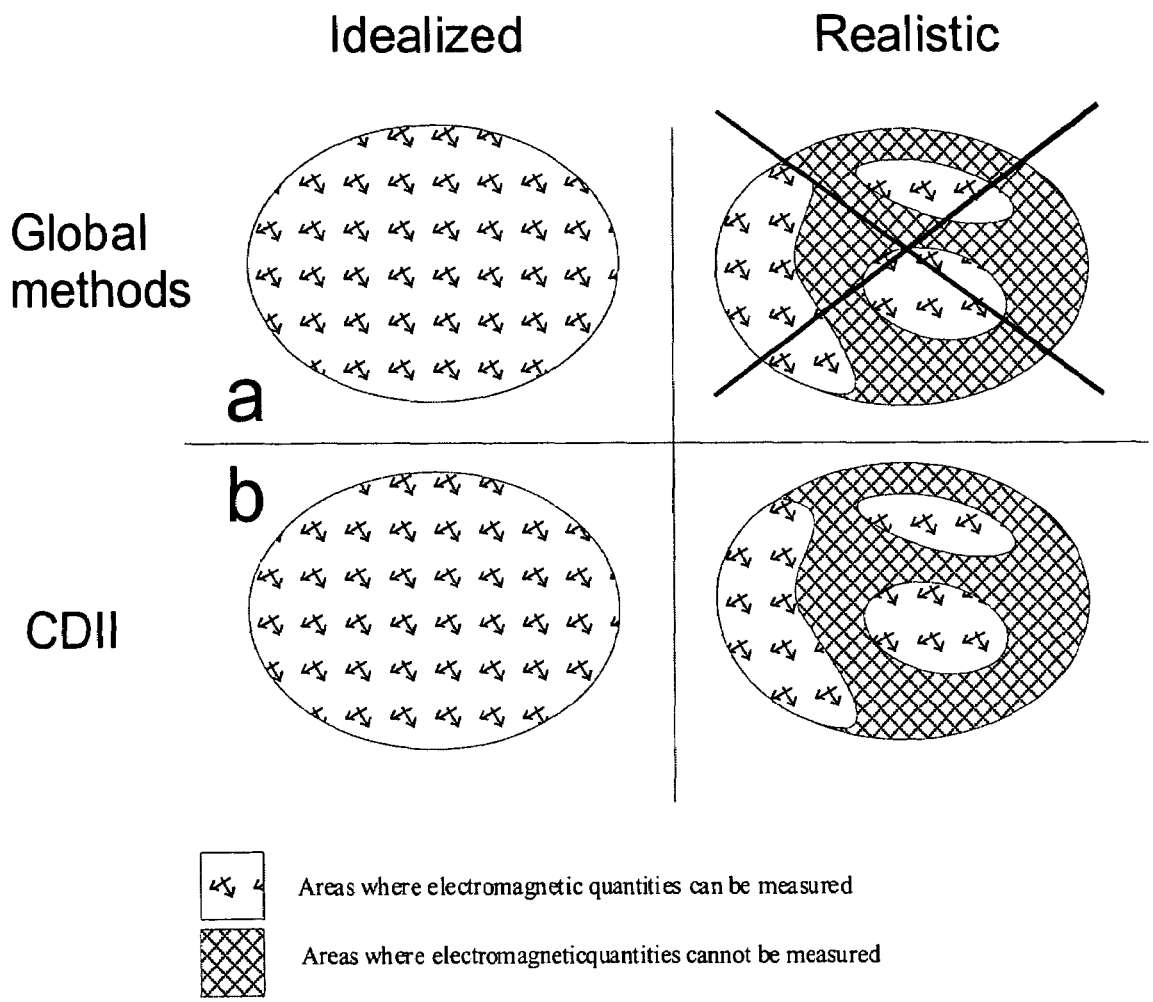
FIG. 1a is a diagrammatic representation of a "global" technique of electrical impedance tomography (EIT) for imaging the electrical impedance of an object non-invasively which requires information from the entire object, even though the region of interest may be limited to a small area.
FIG. 1b is a diagrammatic representation of the method of the present invention, CDII, which is a local measurement technique, and therefore, only requires measurement of information within the region of interest.

CDII is a local measurement technique, and therefore, only requires measurement of information within the region of interest (FIG. 1b). Other "global" techniques require information from the entire object, even though the region of interest may be limited to a small area (FIG. 1a). Therefore, CDII can operate in all situations even where only limited information is available (FIG. 1b). For example, the heart is surrounded by the lung which does not give rise to MR signal. Since CDII is a "local" technique, it is able to proceed with the calculation of conductivity inside the heart while other "global" techniques will fail. In addition, the local calculation of conductivity enables CDII to maintain high spatial resolution and allows the measurement in any sub-regions of the body.

Another benefit of local conductivity measurement is the technique's insensitivity to the physical deformation of the object outside the region of interest. All other approaches require that the shape of the object remain absolutely the same during the procedure. CDII, on the other hand, is not affected by deformation or movement of the object outside the region of interest. Therefore, CDII provides a flexible imaging environment where the object movement is unavoidable (cardiac rhythm, respiratory movement). In fact, the required multiple current density measurements can be made from the said deformation or movement of the object.

Preferred Embodiment

The current density vector information can be acquired using any current measurement techniques. Presently, the preferred method is to use the current density imaging (CDI) technique which utilizes a magnetic resonance imager to measure current density at all points within the object.

Figure 4:
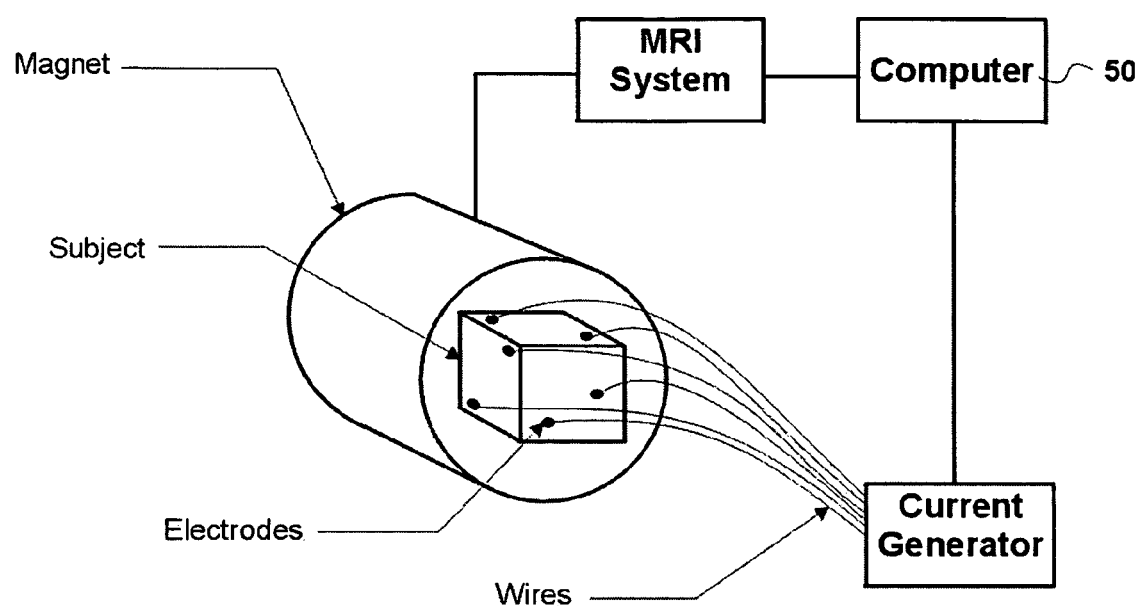
Figure 5:
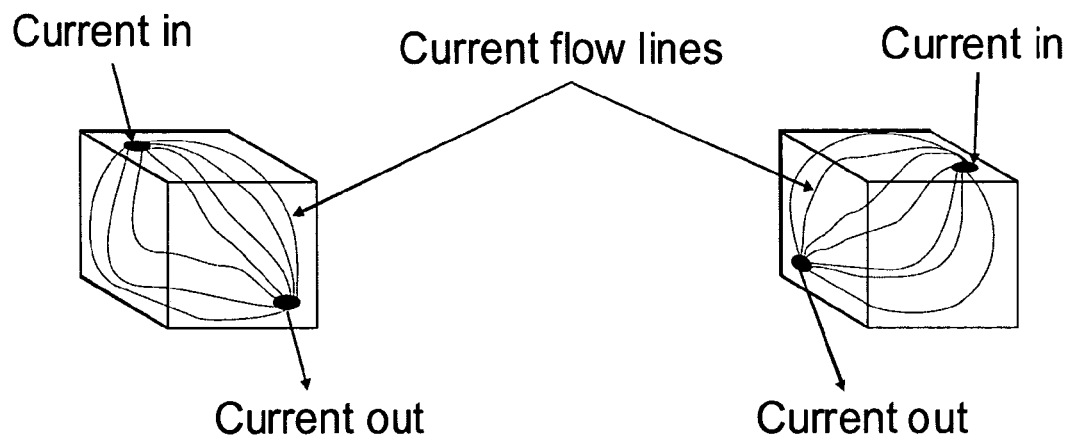
FIG. 5 depicts the requirement in the set-up shown in FIG. 4 where two or more electrodes are placed anywhere on the surface of the object as long as at least two sets of non-parallel current distributions can be created inside the object.

FIG. 4a shows a block diagram of the current density imaging (CDI) technique described in G. C. Scott, M. L. G. Joy, R. L. Armstrong, and R. M. Henkelman, "Measurement of nonuniform current density by magnetic resonance," *IEEE Trans. Med. Imag*, vol. 10, pp. 362-374, 1991 which utilizes a magnetic resonance imager to measure current density at points within the object. The CDI system is set up by placing two or more electrodes on the surface of the object. For the present application, the current electrodes can be placed anywhere on the object as long as at least two sets of nonparallel current distributions can be created inside the object. All wires connecting to the electrodes are fixed to the object to prevent movement. The object is then placed inside a strong magnetic field generated by a magnetic resonance (MR) imager magnet; current is applied by the computer controlled current generator during an MRI pulse imaging sequence as shown in FIG. 4b. The phase image produced by the MRI system is then used to measure a component of the magnetic field created by the applied current. This process is repeated for three orientations of the object. Maxwell's equation, $\vec{J} = \nabla \times \vec{B}/\mu_0$ is then used to calculate the desired current density J.

During the MR imaging, current pulses are applied synchronously with a special imaging sequence (See FIGS. 4b and G. C. Scott, M. L. G. Joy, R. L. Armstrong, and R. M. Henkelman, "Measurement of non-uniform current density by magnetic resonance," *IEEE Trans. Med. Imag*, vol. 10, pp. 362-374, 1991), designed to encode strength of the magnetic field arising from the current flow inside the object. The extra magnetic field component is then encoded in the MR phase image. The phase, θ, depends linearly on the magnetic field component, $B_Z$, produced by the current density, J, and the duration of the current pulse, $T_C$ using the formula $$\theta = \gamma B_Z T_C, \text{ where } \vec{B} = (B_X B_Y B_Z).$$

The resulting MR images are acquired through the use of a typical MR imaging sequence and transferred to a computer. This process is repeated for three orientations of the object. Maxwell's equation, $\vec{J} = \nabla \times \vec{B}/\mu_0$ is then used to calculate the desired current density J. The imaging steps are then repeated to measure the current density vector distribution for other combinations of current electrodes.

In another approach, current flow inside the object can be created through induction from strategically placed coils near the object. By placing coils in close proximity to the object (but not touching the object) and applying electrical current through them, it is possible to induce electrical current flow inside the object. For example, this current inducing coil can be built into the MR system. Therefore, the current application electrodes used in the previous description of the CDII technique can be replaced with appropriately designed current inducing coils, thereby removing any direct mechanical link (i.e. electrodes with wires) to the object.

It will be appreciated by those skilled in the art that any technique, not just that described by Scott, Joy Armstrong and Henkelman [G. C. Scott, M. L. G. Joy, R. L. Armstrong, and R. M. Henkelman, "Measurement of nonuniform current density by magnetic resonance," *IEEE Trans. Med. Imag*, vol. 10, pp. 362-374, 1991] may be used to measure the current density. Roth, for example, describes a technique for computing current density in a region by measuring the magnetic field (produced by a current) at distant points where no currents flow. Similarly Sheltraw and Coutsias describe techniques for solving the problem of determining a current density confined to a volume from measurements of the magnetic and electric fields it produces exterior to that volume. Additionally Lee et all [S. Lee, W. R. Myers, H. L. Grossman, H. M. Cho, Y. R. Chemia, and J. Clarke, "Magnetic gradiometer based on a high-transition temperature superconducting quantum interference device for improved sensitivity of a biosensor," *Applied Physics Letters*, vol. 81, pp. 3094-3096, 2002.] describe a high-transition temperature superconducting quantum interference device (SQUID) that improves the sensitivity of a SQUID-based biosensor used for computing internal naturally occurring bio-currents from external magnetic field measurements made with a superconducting quantum interference device (SQUID). The numerical inverse methods and physical measurement methods used by these authors to compute current density are clearly and publicly disclosed in these published papers. These methods differ from the method of G. C. Scott, M. L. G. Joy, R. L. Armstrong, and R. M. Henkelman, "Measurement of nonuniform current density by magnetic resonance," *IEEE Trans. Med. Imag*, vol. 10, pp. 362-374, 1991 in that they use measurements made at points remote from the regions where the current density is to be computed.

It is also possible to apply sinusoidal current waveforms instead of DC current during CDI procedure. Presently, there are several CDI techniques that can measure sinusoidal current flow up to the Larmor frequency of the imager (63.9 MHz on 1.5 Tesla imager), as disclosed in G. C. Scott, M. L. G. Joy, R. L. Armstrong and R. M. Henkelman. Rotating Frame RF Current Density Imaging, *Magnetic Resonance in Medicine*, 33(3), 355-369, March 1995; Aaron Weinrot, "Variable frequency current density imaging", M. A. Sc. Thesis, University of Toronto, 1999; and Ursa Mikac, Franci Demsar, Katarina Beravs, and Igor Sersa. Magnetic resonance imaging of alternating electric currents. *Magn. Reson. Imag.*, Vol.19, pp. 845-856, 2001.

Therefore, the CDII procedure can measure object conductivities at various frequencies.

The method disclosed herein is advantageous over prior art methods in that it does not require any measurements of electric potentials at the surface of the object. In addition the method of processing the data to create a conductivity image is a completely new, fast, non-iterative method. Furthermore, the present method is the first to allow calculation of conductivity gradients in a specified region when no data is available outside that region. More specifically, the present method does not use measurements of surface potentials and equipotential lines to compute the gradient of electrical potential but rather uses only the current density measurements and uses equation (1) and these measurements to compute the gradient of the logarithm of the conductivity (i.e. the gradient of the logarithm of the "local impedance"). Furthermore, the present method uses the gradient of the logarithm of the conductivity from formula (1) together with standard numerical techniques to find the conductivity distribution and does not use an iterative method to find the conductivity distribution.

Figure 6A:
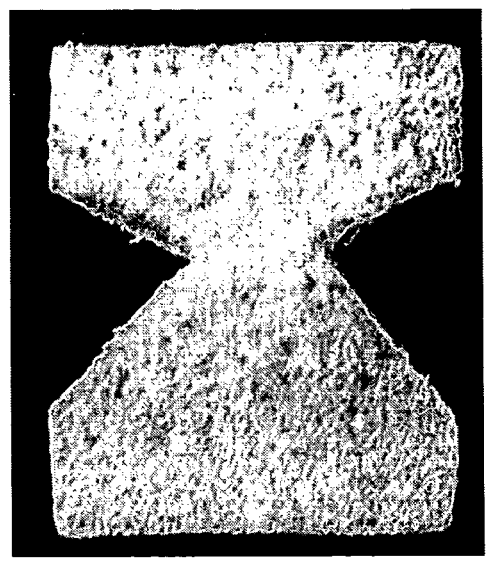
FIG. 6a shows a porous solid developed as a bone matrix phantom for bone cell growth having a pore size of ~1.2 mm in order to test the spatial resolution of the present method.
Figure 6B:
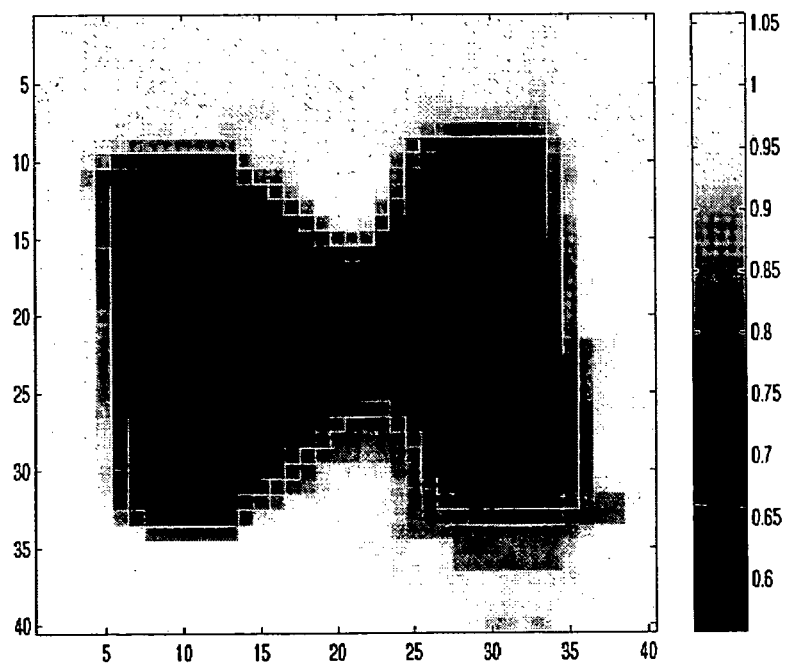
FIG. 6b shows a conductivity image of a slice through the porous bone matrix material of FIG. 6a immersed in saline solution. It is noted that the conductivity of the bone matrix is 65% to 75% of the conductivity of surrounding saline solution.
Figure 6C:
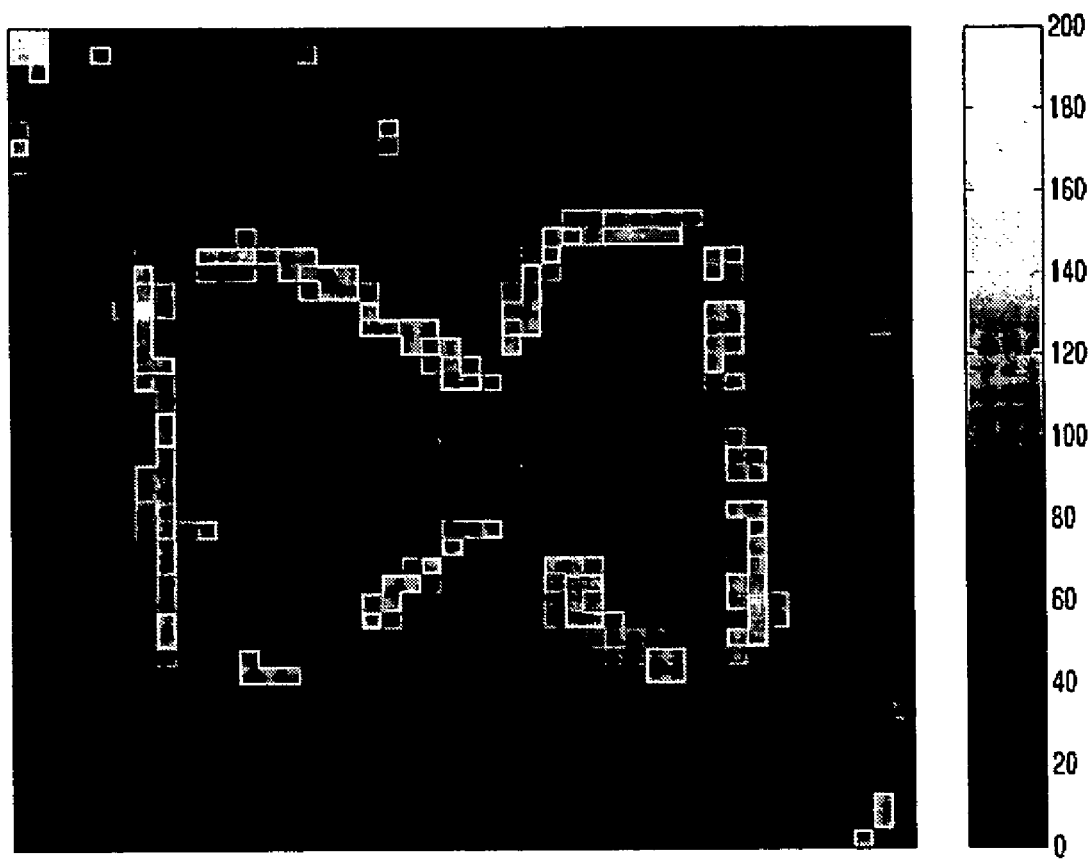
FIG. 6c shows an image made by integrating $\nabla \ln \sigma_R(x,y,z)$ computed using formula (1) so that FIG. 6c is an image of the magnitude of $\nabla \ln \sigma_R(x,y,z)$.

The method was tested on data obtained experimentally from the object shown in FIG. 6a which consisted of a sponge-like material (intended as a scaffold for the growth of bone cells) suspended in salt water. This material had a pore size of ~1.2 mm and was chosen because it was stable in water and could therefore be used to test the spatial resolution. The resulting conductivity image produced using the preferred method disclosed herein is shown in FIG. 6b. FIG. 6c shows an image made by integrating $\nabla \ln \sigma(x,y,z)$ computed using formula (1). FIG. 6c is an image of the magnitude of $\nabla \ln \sigma(x,y,z)$.

SUMMARY AND APPLICATIONS

This invention enables the users to do the following. First, the local logarithmic gradient of conductivity of an object can be measured non-invasively at all points within the object where currents and MR signal exists. Furthermore, this measurement can be performed in any sub-region of interest within the object without the knowledge of the entire object. The absolute conductivity of the object can be calculated from the logarithmic gradient of conductivity by utilizing an a priori knowledge or a surface measurement.

The techniques of the invention may have applications in numerous areas. For example, CDII can be used to as a conductivity contrast imaging tool. Since different tissues (e.g. heart, muscle, etc.) exhibit varying conductivities, it is possible to generate images of the body using conductivity contrast. In addition, some tissues change their conductivity as result of a functional activation (e.g. Cortex, cardiac muscle, etc.) and, therefore, CDII can be employed to measure the activity of these tissues by measuring the changes in conductivity. Furthermore, tissue conductivity changes in certain pathophysiological conditions (eg. Malignant tumor tissue exhibits higher conductivity than the surrounding tissue). Therefore, CDII can be used to monitor tissue activities or their abnormality.

Another application of CDII is to provide an accurate tissue conductivity distribution of the body for the purpose of electromagnetic computer modeling. The computer modeling techniques are widely used in the design of therapeutic devices such as defibrillation, cardioversion and other electrical treatments. The accuracy of these computer simulation techniques are, however, directly related to the available information about the geometry and in-vivo tissue conductivity.

Therefore, CDII can be used to provide both the in-vivo tissue conductivity and the current density distribution to aid in the design of electrical therapeutic devices.

CDII can also be used for the purpose of geological survey of earth's strata. By utilizing earth's magnetic field, it is possible to use CDII technique to obtain high-resolution map of the electrical properties of earth below the surface. Since the cavity of fluids or gases exhibit unique impedance values, CDII can be utilized in exploration of oil and natural gases.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments compassed within the following claims and their equivalents.

What is claimed is:

1. A method of non-invasive imaging of electrical impedance of an object, comprising the steps of:

a) making measurements of at least two nonparallel current density vector fields, $\vec{J}_1(x,y,z)$ and $\vec{J}_2(x,y,z)$, within a region of interest in the object by utilizing an apparatus for inducing current in the object and simultaneously using a magnetic resonance imaging (MRI) system to synchronously apply a magnetic resonance imaging sequence to the object and using image data detected by the MRI system to measure a magnetic field created by the current induced in the object, and using a computer device to calculate said at least two nonparallel current density vector fields, $\vec{J}_1(x,y,z)$ and $\vec{J}_2(x,y,z)$;

b) utilizing a computer device to directly calculate, without iteration a logarithmic gradient of local conductivity, $\nabla \ln \sigma(x, y, z)$, within the region of interest without requiring an electric potential value using a formula $$\nabla \ln \sigma = \frac{(\nabla \times J_2) \cdot (J_1 \times J_2)}{|J_1 \times J_2|^2} J_1 + \frac{(\nabla \times J_1) \cdot (J_2 \times J_1)}{|J_1 \times J_2|^2} J_2 + \frac{(\nabla \times J_1) \cdot J_2}{|J_1 \times J_2|^2} J_1 \times J_2 \quad (1)$$

where $J_1 = \vec{J}_1(x,y,z)$, $J_2 = \vec{J}_2 = (x, y, z)$, and $\nabla \ln \sigma = \nabla \ln \sigma(x,y,z)$, and where $J_1$ and $J_2$ are a pair of measured nonparallel current densities at point $(x,y,z)$ and $\nabla$ denotes a gradient operator; and c) producing a conductivity image based on the calculated logarithmic gradient of local conductivity within the region of interest.

2. The method according to claim 1 further comprising the step of calculating a relative conductivity, $$\sigma_R(x, y, z) = \frac{\sigma(x, y, z)}{\sigma(x_0, y_0, z_0)},$$

between any two points $(x,y,z)$ and $(x_0,y_0,z_0)$ from $\nabla \ln \sigma(x,y,z)$ by integration along any path joining the two points along which $\nabla \ln \sigma(x,y,z)$ has been determined, using a formula for $\sigma_R(x,y,z)$ given by $$\sigma_R(x, y, z) = \exp\left(\int_{(x_0,y_0,z_0)}^{(x,y,z)} \nabla \ln \sigma\right). \quad (2)$$

3. The method according to claim 2 including using the relative conductivity, $\sigma_R(x,y,z)$, to display a conductivity weighted image of the object by selecting an initial point $(x_0,y_0,z_0)$ in the formula (2) and assigning the relative conductivity, $\sigma_R(x,y,z)$, a conductivity of 1.

4. The method according to claim 2 further comprising the step of determining an absolute value of conductivity, $\sigma(x, y, z)$, by the steps of:

determining an absolute value of conductivity, $\sigma(x_0, y_0, z_0)$, at some point in the region of interest; and calculating the absolute conductivity using an equation given by $$\sigma(x, y, z) = \exp\left(\int_{(x_0,y_0,z_0)}^{(x,y,z)} \nabla \ln \sigma\right) \times \sigma(x_0, y_0, z_0). \quad (4)$$

5. The method according to claim 4 wherein the step of determining an absolute value of conductivity, $\sigma(x_0, y_0, z_0)$, at some point in the region of interest includes derivation from either an a priori knowledge of the object, an introduction of an external agent with known conductivity into the object, or a surface measurement of electric potentials.

6. The method according to claim 5 wherein the object is a mammal, and wherein the introduction of an external agent with known conductivity into the object includes the mammal swallowing a pill containing a substance of known conductivity prior to imaging.

7. The method according to claim 1 further comprising the step of calculating the conductivity image of the object using a convolution formula given $$\sigma(r) = \sigma_0 \exp\left\{\int_V \nabla_{r'} G(r, r') \cdot \nabla \ln \sigma(r') d^3 r'\right\} \quad (3)$$

where the conductivity is a known constant value, $\sigma_0$, at a boundary of the region of interest, and G denotes the free space Green's function for the Laplacian.

8. The method according to claim 1 wherein the step of making measurements of at least two nonparallel current density vector fields, $J_1$ and $J_2$, within a region of interest in an object includes:
   a) affixing a sufficient number of current conducting electrodes to a surface of the object so that at least two sets of current distribution are created inside the object, the current conducting electrodes being connected to a current generator;
   b) placing the object inside a magnetic field generated by a magnetic resonance (MR) imager magnet for MR imaging;
   c) during the MR imaging, inducing current flow in an interior of the object by applying current pulses between a first pair of current conductors synchronously with the magnetic resonance imaging sequence which encodes a strength of an extra magnetic field arising from the current flow induced inside the object, the extra magnetic field component being encoded as a part of a complex MR image;
   d) acquiring the resulting complex MR images through the use of a MR imaging sequence and transferring the resulting complex MR images to a computer;
   e) processing the complex MR images to calculate the current density vector field $J_1$; and
   f) repeating steps c), d) and e) at least once more to measure the current density vector field $J_2$ for at least one other combination of current electrodes.

9. The method according to claim 8 wherein the current applied between the electrodes attached to the surface of the object is direct current (DC).

10. The method according to claim 8 wherein the current applied between the electrodes attached to the surface of the object is alternating current (AC).

11. The method according to claim 1 wherein the step of making measurements of at least two current density vector fields, $J_1$ and $J_2$, within a region of interest in the object includes
   a) locating a pre-selected number of current inducing coils at pre-selected locations in close proximity to the object, the current inducing coils being connected to a current source, wherein applying electrical current through the current inducing coils induces at least two sets of current flow distribution inside the object;
   b) placing the object inside a magnetic field generated by a magnetic resonance (MR) imager magnet for MR imaging;
   c) during the MR imaging, inducing current flow in an interior of the object by applying current pulses to a first of the pre-selected number of current inducing coils synchronously with the magnetic resonance imaging sequence which encodes a strength of an extra magnetic field arising from the current flow induced inside the object, the extra magnetic field component being encoded as a part of a complex MR image;
   d) acquiring the resulting complex MR images through the use of a MR imaging sequence and transferring the resulting complex MR images to a computer;
   e) processing the complex MR images to calculate the current density vector field $J_1$; and
   f) repeating steps c), d) and e) at least once more to measure the current density vector field $J_2$ for at least one other of the pre-selected number of current inducing coils.

12. A method of non-invasive imaging of electrical impedance of an object, comprising the steps of:
   a) making measurements of derivatives of at least two nonparallel current density vector fields, $\vec{J}_1(x,y,z)$ and $\vec{J}_2(x,y,z)$ in one direction d within a region of interest in an object when a condition $\partial_d \nabla \sigma = 0$ is satisfied, by utilizing an apparatus for inducing current in the object and simultaneously using a magnetic resonance imaging (MRI) system to synchronously apply a magnetic resonance imaging sequence to the object and using image data detected by the MRI system to measure a magnetic field created by the current induced in the object, and using a computer device to calculate said at least two nonparallel current density vector fields $\vec{J}_1(x,y,z)$ and $\vec{J}_2(x,y,z)$;
   b) utilizing a computer device to directly calculate, without iteration, the logarithmic gradient of local conductivity, $\nabla \ln \sigma(x,y,z)$, at that point within the region of interest without requiring an electric potential value, using a formula $$\nabla \ln\sigma = \frac{(\nabla \times \partial_d J_2)\cdot(\partial_d J_1 \times \partial_d J_2)}{|\partial_d J_1 \times \partial_d J_2|^2}\partial_d J_1 + \frac{(\nabla \times \partial_d J_1)\cdot(\partial_d J_2 \times \partial_d J_1)}{|\partial_d J_1 \times \partial_d J_2|^2}\partial_d J_2 + \frac{(\nabla \times \partial_d J_1)\cdot \partial_d J_2}{|\partial_d J_1 \times \partial_d J_2|^2}\partial_d J_1 \times \partial_d J_2 \quad (5)$$

where $J_1 = \vec{J}_1(x,y,z)$, $J_2 = \vec{J}_2(x,y,z)$, and $\nabla\ln\sigma = \nabla \ln\sigma(x,y,z)$, and where $\partial_d$ denotes a directional derivative in a direction d, and $\partial J_1$ and $\partial_d J_2$ are a pair of measured derivatives of the current density vector fields in the direction d at a point (x,y,z), and $\nabla$ denotes a gradient operator; and
   c) producing a conductivity image based on the calculated logarithmic gradient of local conductivity within the region of interest.

13. The method according to claim 12 further comprising the step of calculating a relative conductivity, $$\sigma_R(x, y, z) = \frac{\sigma(x, y, z)}{\sigma(x_0, y_0, z_0)},$$

between any two points (x,y,z) and $(x_0,y_0,z_0)$ from $\nabla \ln \sigma(x,y,z)$ by integration along any path joining the two points along which $\nabla \ln \sigma(x,y,z)$ has been determined, using a formula for $\sigma_R(x,y,z)$ given by $$\sigma_R(x, y, z) = \exp\left(\int_{(x_0,y_0,z_0)}^{(x,y,z)} \nabla \ln\sigma\right). \quad (2)$$

14. The method according to claim 13 including using the relative conductivity, $\sigma_R(x,y,z)$, to display a conductivity weighted image of the object by selecting an initial point $(x_0,y_0,z_0)$ in the formula (2) and assigning the relative conductivity, $\sigma_R(x,y,z)$, a conductivity of 1.

15. The method according to claim 13 further comprising the step of determining an absolute value of conductivity, $\sigma(x, y, z)$, by the steps of:
   determining an absolute value of conductivity, $\sigma(x_0,y_0,z_0)$, at some point in the region of interes; and
   calculating the absolute conductivity using an equation given by $$\sigma(x, y, z) = \exp\left(\int_{(x_0,y_0,z_0)}^{(x,y,z)} \nabla \ln \sigma\right) \times \sigma(x_0, y_0, z_0). \quad (4)$$

16. The method according to claim 15 wherein the step of determining an absolute value of conductivity, $\sigma(x_0,y_0,z_0)$, at some point in the region of interest includes derivation from either an a priori knowledge of the object, an introduction of an external agent with known conductivity into the object, or surface measurement of potentials.

17. The method according to claim 15 wherein the object is a mammal, and wherein the introduction of an external agent with known conductivity into the object includes the mammal swallowing a pill containing a substance of known conductivity prior to imaging.

18. The method according to claim 12 further comprising the step of calculating the conductivity image of the object using a convolution formula given by $$\sigma(r) = \sigma_0 \exp\left\{\int_V \nabla_{r'} G(r, r') \cdot \nabla \ln \sigma(r') d^3 r'\right\} \quad (3)$$

wherein the conductivity is a known constant value, $\sigma_0$, at a boundary of the region of interest, and G denotes the free space Green's function for the Laplacian.

19. A method of non-invasive imaging of electrical impedance of an object, comprising the steps of:
 a) affixing a sufficient number of current conducting electrodes to a surface of the object so that at least two sets of current distribution are created inside the object, the current conducting electrodes being connected to a current generator;
 b) placing the object inside a magnetic field generated by a magnetic resonance (MR) imager magnet for MR imaging;
 c) during the MR imaging, inducing current flow in an interior of the object by applying current pulses between a first pair of current conductors synchronously with a magnetic resonance imaging sequence which encodes a strength of an extra magnetic field arising from the current flow induced inside the object, the extra magnetic field component being encoded as a part of a complex MR image;
 d) acquiring the resulting complex MR images and transferring the resulting complex MR images to a computer;
 e) processing the complex MR images to calculate a current density vector field $\vec{J}_1(x,y,z)$ within a region of interest in the object;
 f) repeating steps c), d) and e) at least once more to measure the current density vector field $\vec{J}_2(x,y,z)$ within the region of interest for at least one other combination of current electrodes; and
 g) utilizing a computer device to directly calculate, without iteration, a logarithmic gradient of local conductivity, $\nabla \ln \sigma(x,y,z)$, within the region of interest without requiring an electric potential value, using a formula $$\nabla \ln \sigma = \quad (1)$$
$$\frac{(\nabla \times J_2) \cdot (J_1 \times J_2)}{|J_1 \times J_2|^2} J_1 + \frac{(\nabla \times J_1) \cdot (J_2 \times J_1)}{|J_1 \times J_2|^2} J_2 + \frac{(\nabla \times J_1) \cdot J_2}{|J_1 \times J_2|^2} J_1 \times J_2$$

where $J_1 = \vec{J}_1(x, y, z)$, $J_2 = \vec{J}_2(x,y,z)$, and $\nabla \ln \sigma = \nabla \ln \sigma(x,y,z)$, and where $\vec{J}_1(x,y,z)$ and $\vec{J}_2(x,y,z)$ are a pair of measured nonparallel current densities at point (x,y,z) and $\nabla$ denotes a gradient operator; and
 h) producing a conductivity image based on the calculated logarithmic gradient of local conductivity within the region of interest.

20. The method according to claim 19 further comprising the step of calculating a relative conductivity, $$\sigma_R(x, y, z) = \frac{\sigma(x, y, z)}{\sigma(x_0, y_0, z_0)},$$

between any two points (x,y,z) and $(x_0,y_0,z_0)$ from $\nabla \ln \sigma(x,y,z)$ by integration along any path joining the two points along which $\nabla \ln \sigma(x,y,z)$ has been determined, using a formula for $\sigma_R(x,y,z)$ given by $$\sigma_R(x, y, z) = \exp\left(\sum_{(x_0,y_0,z_0)}^{(x,y,z)} \nabla \ln \sigma\right). \quad (2)$$

21. The method according to claim 20 including using the relative conductivity, $\sigma_R(x,y,z)$, to display a conductivity weighted image of the object by selecting an initial point $(x_0,y_0,z_0)$ in the formula (2) and assigning the relative conductivity, $\sigma_R(x,y,z)$, a conductivity of 1.

22. The method according to claim 20 further comprising the step of determining an absolute value of conductivity, $\sigma(x, y, z)$, by the steps of:
 determining an absolute value of conductivity, $\sigma(x_0,y_0,z_0)$, at some point in the region of interest, and
 calculating the absolute conductivity using an equation given by $$\sigma(x, y, z) = \exp\left(\sum_{(x_0,y_0,z_0)}^{(x,y,z)} \nabla \ln \sigma\right) \times \sigma(x_0, y_0, z_0). \quad (4)$$

23. The method according to claim 22 wherein the step of determining an absolute value of conductivity, $\sigma(x_0,y_0,z_0)$, at some point in the region of interest includes derivation from either an a priori knowledge of the object, an introduction of an external agent with known conductivity into the object, or a surface measurement of potentials.

24. The method according to claim 22 wherein the object is a mammal, and wherein the introduction of an external agent with known conductivity into the object includes the mammal swallowing a pill containing a substance of known conductivity prior to imaging.

25. The method according to claim 19 further comprising the step of calculating the conductivity image of the object using a convolution formula given by $$\sigma(r) = \sigma_0 \exp\left\{\int_V \nabla_{r'} G(r, r') \cdot \nabla \ln \sigma(r') d^3 r'\right\} \quad (3)$$

wherein the conductivity is a known constant value, $\sigma_0$, at a boundary of the region of interest, and G denotes the free space Green's function for the Laplacian.

26. The method according to claim 19 wherein the current applied between the electrodes attached to the surface of the object is direct current (DC).

27. The method according to claim 19 wherein the current applied between the electrodes attached to the surface of the object is alternating current (AC).

* * * * *